United States Patent [19]

Kojima et al.

[11] Patent Number: 4,688,015

[45] Date of Patent: Aug. 18, 1987

[54] GAS SENSOR WITH CERAMICS SUBSTRATE HAVING SURFACE-CARRIED CERAMICS PARTICLES

[75] Inventors: Takao Kojima, Nagoya; Akira Nakano, Inuyama; Toshitaka Matsuura, Komaki; Akio Takami, Konan, all of Japan

[73] Assignee: NGK Spark Plug Co., Ltd., Nagoya, Japan

[21] Appl. No.: 664,872

[22] Filed: Oct. 25, 1984

[30] Foreign Application Priority Data

Oct. 28, 1983 [JP] Japan .............................. 58-203222
Mar. 28, 1984 [JP] Japan .............................. 59-60048
Sep. 4, 1984 [JP] Japan .............................. 59-183818

[51] Int. Cl.$^4$ ............................................. H01L 7/00
[52] U.S. Cl. ..................................... 338/34; 338/310; 338/314
[58] Field of Search .................... 338/34, 310, 314; 264/60, 61, 62, 67; 361/321, 322; 501/20; 427/102, 103, 101, 126.1, 126.2, 126.3, 123; 156/89

[56] References Cited

U.S. PATENT DOCUMENTS

| | | | |
|---|---|---|---|
| 4,333,067 | 6/1982 | Kugimiya et al. | 338/34 |
| 4,477,487 | 10/1984 | Kojima et al. | 427/123 |
| 4,507,643 | 3/1985 | Sunano et al. | 338/34 |
| 4,536,241 | 8/1985 | Logothetis et al. | 338/34 X |
| 4,592,967 | 6/1986 | Komatsu et al. | 338/34 X |
| 4,614,669 | 9/1986 | Yannopoulos | 427/87 |

FOREIGN PATENT DOCUMENTS 0001509 4/1979 European Pat. Off. .............. 338/34

OTHER PUBLICATIONS

"Homogeneous Semiconducting Gas Sensors," by G. Heiland, Sensors and Actuators, 2, 1982, pp. 343–359.

Primary Examiner—E. A. Goldberg
Assistant Examiner—M. M. Lateef
Attorney, Agent, or Firm—Fleit, Jacobson, Cohn & Price

[57] ABSTRACT

A roughened surface is formed on an insulating ceramics substrate having an electrode pattern by bonding or partially thrusting ceramics particles to or in the substrate, and a gas-sensitive metal oxide thick film is firmly bonded to the roughened surface.

3 Claims, 16 Drawing Figures

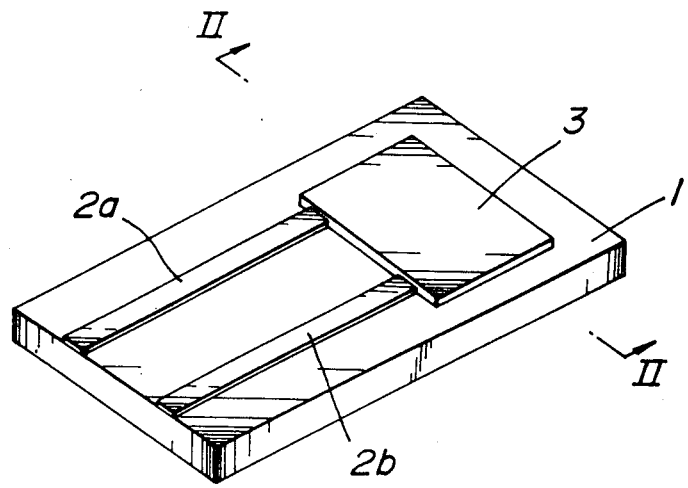
FIG._1 PRIOR ART
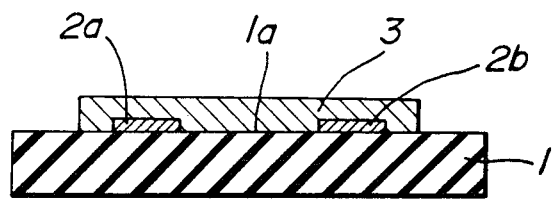
FIG._2 PRIOR ART

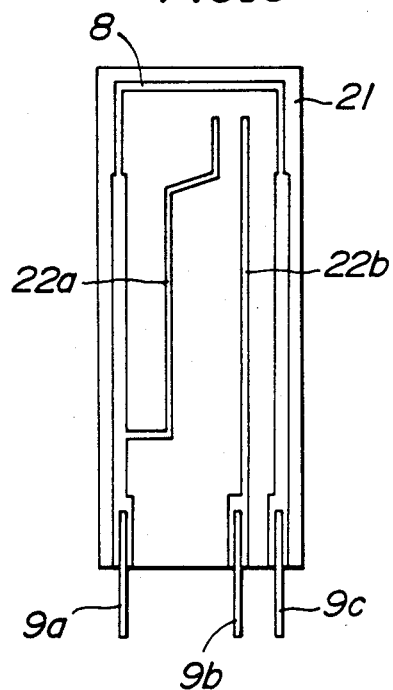
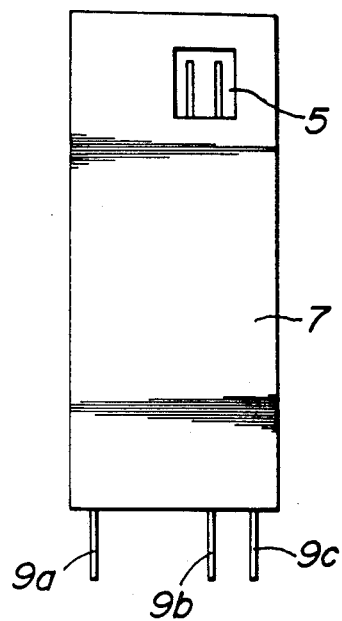
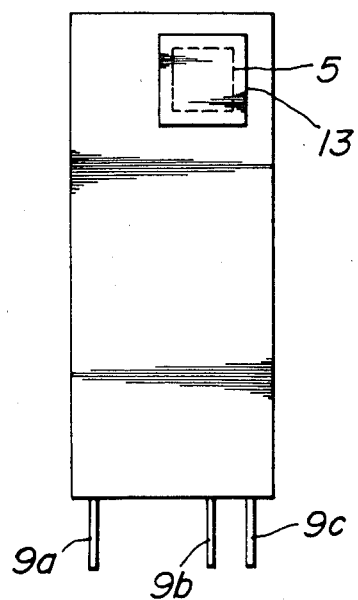

FIG._10A
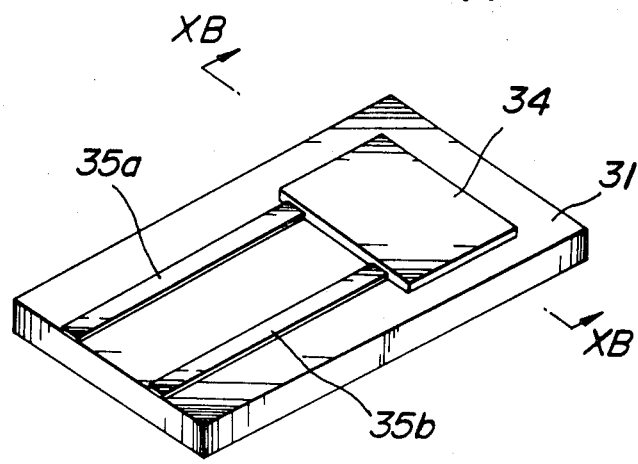
FIG._10B
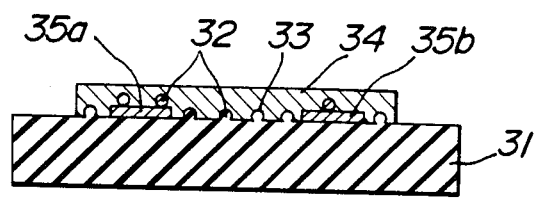
FIG._11
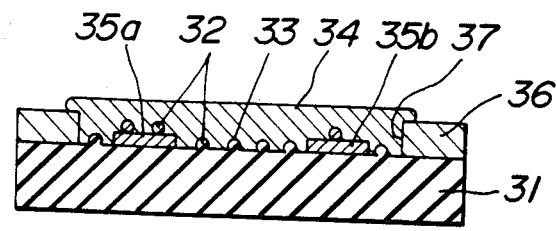

GAS SENSOR WITH CERAMICS SUBSTRATE HAVING SURFACE-CARRIED CERAMICS PARTICLES

BACKGROUND OF THE INVENTION

1. Field of the Invention

This invention relates to a gas sensor of thick film type and to a method of producing a gas sensor having a substrate and a thick film sensor element firmly bonded to the substrate.

Application of the thick film techniques has been expanding recently with the progress of the so-called hybrid techniques. For instance, the thick film techniques are applied to production of a sensor by forming a metal oxide thick film on a ceramics substrate, which metal oxide has a temperature-sensitive or gas concentration sensitive resistance; production of a ceramic capacitor by forming a metal oxide thick film on a ceramics substrate, which metal oxide has a high dielectric constant; formation of a protective thick film such as alumina ($Al_2O_3$) thick film on a substrate of silicon nitride ($Si_3N_4$) or the like for improving the corrosion-resistivity or acid-resistivity of the substrate.

The invention provides a remarkable improvement in the bond between an insulating ceramics substrate and a thick film formed thereon, which improvement is applicable to various kinds of thick films.

2. Description of the Prior Art

FIG. 1 shows a typical conventional thick film gas sensor element formed on a substrate. More specifically, an insulating ceramics substrate 1 carries electrodes 2a and 2b of a certain desired configuration formed thereon by printing. A sensor element 3 is formed on the substrate 1 by printing a thick film of paste thereon, which paste mainly consists of gas-sensitive metal oxide, and firing the thus printed thick film of paste. The sensor thus formed has various advantages; for instance, the sensor element 3 is thin and has excellent response characteristics, and a heater indispensable to many sensors can be formed on the same substrate simply by printing a thick film heater resistor thereon.

The above sensor, however, has a disadvantage in that the bond between the substrate 1 and the sensor element 3 is comparatively weak, because the top surface 1a of the above substrate 1 to which the sensor element 3 is fired is flat and smooth as shown in the sectional view of FIG. 2 taken along the line II—II of FIG. 1. When the gas sensor is exposed to frequent temperature change over a wide range such as that experienced in automobile engine exhaust gas, thermal strain is caused in the sensor element 3 due to the difference of coefficient of thermal expansion between the substrate 1 and the sensor element 3, and such thermal strain tends to cause separation of the sensor element 3 from the substrate 1. To reduce the risk of such separation, the substrate 1 may be made by using material consisting of ceramics particles with a comparatively large diameter, so as to make the surface thereof uneven. On the other hand, the use of large ceramics particles is apt to deteriorate the properties of the substrate 1, such as electric insulation, mechanical strength, and the like.

It has been proposed to use a bond-improving additive, such as glass, in the material of the thick film of certain kind by D. I. Herbst et al in "Int. Microelectronics Symp. (1971) 4.7" and by M. V. Coleman et al in "Proc. Inst. Electro. Radio Eng. Conf. (1976) [31] 1–16". However, the use of an additive often results in inevitable change of the properties of the thick film itself.

As another method for improving the bond, W. H. Kohl suggested to select such combination of a substrate and a thick film wherein they have similar coefficients of thermal expansion, in the book entitled "Materials and Techniques for Vacuum Devices" (1967) Reinhold Pub. at page 391. This combination is effective in reducing the thermal strain and preventing the separation even if the adhesion between the thick film and the substrate is not so strong. However, this combination does not provide sufficient impact strength.

Further, it has been repeatedly attempted to improve the bond of the thick film by roughening the surface of the substrate therefor; for instance, by grinding the substrate surface by grains of large diameter or by shot blasting, as well known in the art. It has been also attempted to cover the substrate surface with crystalline particles of large diameter, so as to make use of projections formed thereby, but a satisfactory bond was not obtained due to the difference in the sintering characteristics between the crystalline particles and the substrate caused by the difference in crystal grain size therebetween. Besides, in the covering with the crystalline particles, it was impossible to provide a homogeneously controlled unevenness. In general, the conventional roughening of the substrate surface did not provide sufficient bonding strength for films thicker than 10 $\mu$m. The above grinding or shot blasting for roughening the substrate surface hurts the substrate in the end, so that its tends to weaken the strength of the substrate.

In short, there has not been any method suitable for improving the bond of a thick film, especially a functional semiconductor thick film, with a substrate therefor.

SUMMARY OF THE INVENTION

After a number of studies and experiments, the inventors found that if particles are bonded to the film-receiving surface of a substrate so as to roughen that surface by formulating projections thereon and if a sensor element thick film is formed on the thus roughened surface of the substrate, the bond between the sensor element and the substrate is strengthened, and the risk of separation of the sensor element from the substrate is minimized.

The present invention is based on the above finding of the inventors, and an object of the present invention is to obviate the above-mentioned shortcomings of the prior art by providing an improved gas sensor. A gas sensor according to the invention comprises an insulating sintered ceramics substrate, an electrode means in the form of thick film formed on a surface of the substrate, granulated ceramics particles integrally bonded to said surface of the substrate in the vicinity of said electrode means, said granulated ceramics particles having a mean diameter of at least 5 $\mu$m or more and a maximum diameter of not larger than 500 $\mu$m or less before being sintered, and a sensor element thick film firmly bonded to said surface of the substrate by said granulated ceramics particles in such a manner that said sensor element is electrically connected to said electrode means.

Another object of the invention is to provide a method for producing a gas sensor, in which method a green sheet consisting of insulating ceramics powder and organic binder is prepared. A thick film for an electrode means of a certain pattern is printed on a surface of the green sheet. Granulated ceramics particles are scattered on said surface of the green sheet in the vicinity of said electrode means, said granulated ceramics particles having a mean diameter of at least 5 $\mu$m or more and a maximum diameter of not larger than 500 $\mu$m or less. After sintering the green sheet with the electrode means and the thus scattered ceramics particles, another thick film of paste mainly consisting of gas-sensitive metal oxide for a sensor element is printed on the thus scattered ceramics particles. The metal oxide thick film is then fired so as to produce the desired gas sensor.

Another object of the invention is to provide a futher development of the above invention, in which the bond between the sensor element and the substrate is improved by thrusting the granulated ceramics particles into the surface portion of the green sheet by one-twentieth to one-fourth of their mean diameter.

A further object of the invention is to provide a ceramics substrate carrying a metal oxide thick film, which thick film can be 10 $\mu$m in thickness or thicker than 10 $\mu$m. In this case, a roughened surface is formed on a substrate by scattering ceramics particles on the substrate while partially thrusting them into said substrate, and a metal oxide thick film is sintered onto said roughened surface so as to fill up interstices among projections thereof.

To fulfil the above objects; a ceramics substrate carrying a thick film of metal oxide is made by forming a roughened surface on a ceramics substrate by scattering and partially thrusting sintered ceramics particles into a surface of the ceramics substrate, and applying and firing a thick film of metal oxide on the roughened surface of the substrate in such a manner that the thick film fills up interstices among projections on the roughened surface.

The insulating ceramics substrate to be used in the present invention is made of alumina, beryllium, forsterite, zirconia, oxides of metals such as barium titanate, ferrite, and the like, non-oxides such as silicon nitride, aluminium nitride, and the like.

The ceramics particles to be used for ensuring firm bondage of the thick film of metal oxide to the surface of the insulating ceramics substrate are preferably made of a material which is same as or similar to that of the substrate. However, it is of course possible to use different materials for the sintered particles and the substrate, as long as their sintering characteristics are similar to each other.

The ceramics particles to be scattered on a surface of the substrate are at first granulated. Preferably, the granulated ceramics particles have a mean diameter of at least 5 $\mu$m or larger than 5 $\mu$m, more preferably at least 50 $\mu$m and not over than 200 $\mu$m, and a maximum diameter of not larger than 500 $\mu$m, more preferably not larger than 300 $\mu$m, before being sintered.

If the mean diameter of the granulated ceramics particles is smaller than 5 $\mu$m, it is difficult to achieve such a bondage between the substrate and the thick film formed thereon which is strong enough for ensuring sufficient bonding strength in the case of thick films. On the other hand, if the maximum diameter of the granulated ceramics particles is larger than 500 $\mu$m, it becomes difficult to uniformly form thick film, such as a sensor element thick film, by a conventional method such as printing, and hence a dispersion of the thickness is likely to occur in the thick films such as sensor element thick films.

Preferably, the granulated ceramics particles are partially thrusted into the surface portion of the substrate by a depth corresponding to one-twentieth to one-fourth of the mean diameter thereof. If the thrusting is less than one-twentieth of the mean diameter, sufficient improvement of the bondage of the particles to the substrate by such thrusting becomes hard to achieve. On the other hand, if the ceramics particles are thrusted too deeply into the substrate in excess of one-quarter of the mean diameter, the work to achieve such deep thrust in a uniform fashion becomes difficult and it becomes difficult to provide sufficient hook action between such ceramics particles and a thick film such as a sensor element thick film formed thereon.

As to the density of the scattered, and preferably thrusted, sintered ceramics particles, the ratio of the area of the insulating ceramics substrate surface uncovered by the ceramics particles in a zone where the ceramics particles are scattered, as seen at right angles to the plane of the substrate, to the net area of the ceramics particles in said zone as seen at right angles to the plane of the substrate (to be referred to as the "coverage ratio", hereinafter) is preferably in a range of 1:4 to 4:1. The optimal coverage ratio is 1:1, and a suitable value of the coverage ratio can be selected depending on the actual conditions of each application.

The preferable relationship between the material of the ceramics particle to be scattered and the material of the insulating ceramics substrate has been pointed out in the foregoing. In addition, it may be supplemented here that the most preferable material of the ceramics particles is alumina from the standpoint of mechanical strength, heat resistivity, insulating strength, and economy, but mullite, zirconia, and spinel may be also used as second suitable material for the ceramics particles.

Typical examples of the method for producing the ceramics substrate carrying a metal oxide thick film according to the present invention are as follows:

At first, a green sheet for the insulating ceramics substrate is prepared by making a slurry which is a mixture of ceramics powder and an organic binder in an organic solvent, and shaping the slurry into a green sheet by a method using a doctor blade or the like.

An electrode pattern of a certain configuration, such as comb-shaped pattern or spiral pattern, is printed on a surface of the thus prepared green sheet in the form of a thick film of metallic paste. The metallic paste contains platinum (Pt), palladium (Pd), rhodium (Rh), gold (Au), or an alloy of any of the above metals. In the present invention, it is preferred but not required to form the electrode pattern immediately after the preparation of the green sheet, and in fact, the electrode pattern may be formed after the roughening of the substrate surface as will be described hereinafter. When the present invention is applied to simple formation of a coating on the ceramics substrate by using material foreign to that of the substrate, the step of providing the electrode pattern can of course be eliminated.

Separately, ceramics particles with diameters in the above-mentioned range are granulated by a conventional method or by using a spray dryer. If desired, the thus granulated ceramics particles may be hardened to facilitate the handling thereof by heating them at a temperature below the starting point of sintering. The ceramics particles as granulated or after the above heating are scattered on a specific zone of the substrate surface, such as the vicinity of the electrode pattern, so as to cover the specific zone of the substrate surface at the above-mentioned range of the coverage ratio. The ceramics particles thus scattered may be partially thrusted into the surface portion of the ceramics substrate, for instance, by pressing them with a flat board. Preferably a cushion sheet is inserted between the ceramics particles and the pressing flat board, so as to keep the shape of the granulated ceramics particles intact.

The method to form the ceramics particles as partially and integrally thrusted into the surface portion of the ceramics substrate is not limited to the above pressing by the flat board. For instance, a suspension containing the above-mentioned granulated ceramics particles and binding minute particles may be prepared by mixing them in a suitable suspending solvent, and the thus prepared suspension may be spread on the green sheet of the ceramics substrate. The green sheet with the suspension is held still until the binding minute particles precipitate on the surface of the green sheet so as to provide footings for the ceramics particles with a desired depth. Then, the green sheet with the suspension having such precipitation may be sintered so as to form the ceramics substrate with the ceramics particles partially thrusted into the surface portion of the substrate. Alternatively, a suitable solvent may be spread on the green sheet and the granulated ceramics particles may be simply scattered on the solvent coated surface of the ceramics substrate.

The green sheet with the granulated ceramics particles scattered thereon is sintered by heating it at a temperature suitable therefor, so as to integrally bond the ceramics particles to the ceramics substrate while partially thrusting the ceramics particles into the surface portion of the substrate. A semiconductor thick film for a sensor element is applied to that surface portion of the ceramics substrate having the ceramics particles scattered thereon, either by printing or casting of a paste for the thick film. The paste for the thick film mainly consists of gas-sensitive metal oxide powder, such as powder of titania ($TiO_2$), tin oxide ($SNO_2$), zinc oxide (ZnO), iron oxide ($Fe_2O_3$), and the like. If necessary, the ingredients of the above-mentioned metallic paste may be added to the paste for the thick film. Then, the semiconductor thick film is fired, so as to produce the desired ceramics substrate carrying the thick film firmly bonded thereto.

Accordingly, the thick film for a sensor element is bonded to the ceramics substrate by intruding lower portions thereof into interstices among projections on the surface of the ceramics substrate, which projections are formed by ceramics particles uniformly scattered on and integrally sintered to, preferably partially thrusted into, the ceramics substrate, and the thick film with such intruding portions is fired, so that the bondage of the thick film to the ceramics substrate is very strong. Besides, the ceramics particles holding the above-mentioned intruding lower portions of the thick film are also bonded to the ceramics substrate very strongly. Whereby, a highly stable function of the thick film, such as the function of gas sensing, is ensured in the ceramics substrate carrying the thick film according to the present invention.

BRIEF DESCRIPTION OF THE DRAWINGS

For a better understanding of the invention, reference is made to the accompanying drawings, in which:

FIG. 1 is a schematic perspective view of a conventional gas sensor;

FIG. 2 is a schematic sectional view taken along the line II—II of FIG. 1;

FIG. 5 is a schematic plan view of a green sheet for a ceramics substrate, which green sheet is provided with an electrode pattern and a heater resistor pattern in the first stage of a method for producing a gas sensor;

FIG. 6 is a schematic plan view of the green sheet for ceramics substrate and another green sheet overlaid thereon in an intermediate stage of the method for producing a gas sensor according to the present invention;

FIG. 7 is a schematic plan view of a gas sensor produced by the method of the invention, a cross-section of which is shown in FIG. 2;

Figure 9A:
Figure 9B:
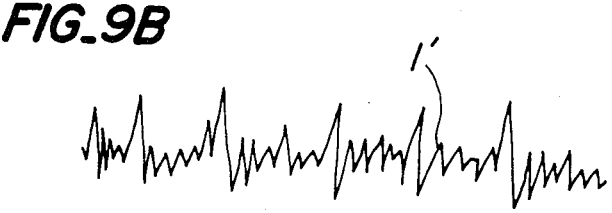
Figure 9C:
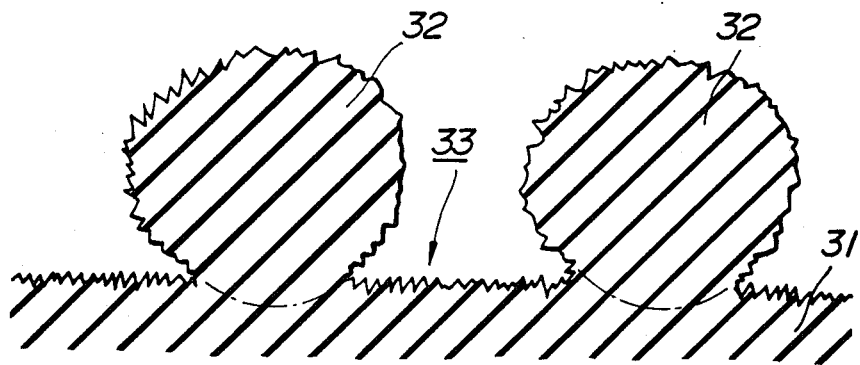

Views (a), (b) and (c) of FIG. 9 show considerably exaggerated fragmental cross-sections of ceramics substrates with and without roughening and with ceramics particles partially thrusted therein;

FIG. 10A is a schematic perspective view of an embodiment of the gas sensor according to the present invention;

FIG. 10B is a sectional view taken along the line XB—XB of FIG. 10A; and

FIG. 11 is a schematic sectional view of another embodiment of the gas sensor according to the present invention.

Throughout different views of the drawings, 1 is a ceramics substrate, 1a is a substrate surface, 2a, 2b are electrodes forming an electrode pattern, 3 is a sensor element, 4 represents ceramics particles, 5 is an opening, 7 is a green sheet, 8 is a resistive heater pattern, 9a, 9b, 9c are terminals made of platinum lead wires, 11 is a substrate, 12a, 12b are electrodes forming an electrode pattern, 13 is a sensor element, 21 is a green sheet, 22a, 22b are electrodes forming an electrode pattern, 31 is an insulating ceramics substrate, 32 represents sintered ceramics particles, 33 is a roughened surface, 34 is a fired thick film, 35a, 35b are electrodes forming an electrode pattern, 36 is a windowed protective sheet, and 37 is a window opening.

DESCRIPTION OF THE PREFERRED EMBODIMENT

The invention will be described in detail by referring to preferred embodiments illustrated in the drawings.

Figure 3:
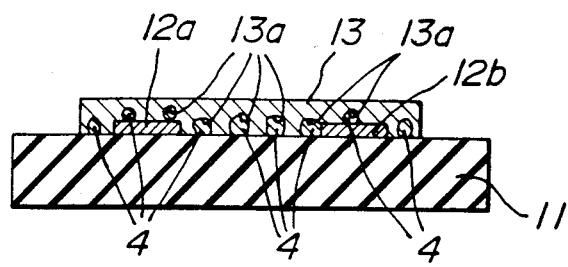
FIG. 3 is a schematic sectional view of a gas sensor according to the present invention.

Referring to FIG. 3 showing a schematic sectional view of the bondage between a sensor element and a substrate in a gas sensor of the invention, an insulating sintered ceramics substrate 11 has thick film electrodes 12a and 12b formed on one side surface thereof so as to form an electrode pattern. Ceramics particles 4 are scattered on and integrally bonded to the above one side surface of the ceramics substrate 11 in the vicinity of the electrodes 12a, 12b. A sensor element 13 in the form of thick film is printed on the above one side surface of the ceramics substrate 11 so as to be electrically connected to the electrodes 12a and 12b and firmly bonded to the substrate 11 through the ceramics particles 4.

The sensor element 13 is very strongly bonded to the ceramics substrate 11 in the gas sensor of the invention due to the following reasons. Firstly, the ceramics particles 4 bonded to the substrate provide a roughened surface to the substrate, so as to increase the contact area between the sensor element 13 and the ceramics substrate 11. Secondly, the granular ceramics particle 4 engage recesses 13a at the bottom surface of the sensor element 13 so as to bring about hook action therebetween. The ceramics particles 4 are prepared in the form of granular secondary particles of which diameters fall in the above-mentioned range before being sintered; namely, the mean diameter of the ceramics particles 4 before sintering must be at least 5 $\mu$m or more and their maximum diameter before sintering must be not larger than 500 $\mu$m or less. The roughness of the substrate surface produced by such ceramics particles 4 is much higher than that of regular substrate.

If the mean diameter of the ceramics particles 4 is smaller than 5 $\mu$m, sufficient roughness for improving the bondage cannot be achieved, while presence of excessively large ceramic particles 4 with a diameter of larger than 500 $\mu$m tends to hamper the formation of uniform thickness in printing the thick film for the sensor element 13. Besides, excessively large ceramics particles 4 tend to cause a large dispersion. A more preferable range of the size of the ceramics particles 4 is 50–200 $\mu$m.

As to the amount of the ceramics particles 4 to be used, the above-mentioned range of the coverage ratio should be referred to; more particularly, the coverage ratio (A/B) of the surface area (A) of the insulating ceramics substrate 11 uncovered by the ceramics particles 4 in a zone where the ceramics particles 4 are scattered, as seen at right angles to the plane of the substrate 11, to the net area (B) of the ceramics particles 4 in said zone as seen at right angles to the plane of the substrate 11 should be in a range of 1:4 to 4:1. The preferable value of the coverage ratio is about 1:1.

The ceramics particles 4 are preferably made of the same material as that of the ceramics substrate 1 from the standpoint of simplicity in production. However, other insulating ceramics material may be used for the ceramics particles 4, provided that desired effect of the invention is achieved thereby. More specifically, it may be pointed out here that the most preferable material of the ceramics particles 4 is alumina from the standpoint of mechanical strength, heat resistivity, insulating strength, and economy, but mullite, zirconia, and spinel may be also used as suitable material for the ceramics particles 4.

A method for producing the gas sensor according to the invention will be described now. A green sheet for the insulating ceramics substrate 11 is prepared by making a slurry which is a mixture of electrically insulating ceramics powder and an organic binder in an organic solvent, and shaping the slurry into the green sheet by a method using a doctor blade or the like. Thick films for the electrodes 12a and 12b forming an electrode pattern are printed on a surface of the thus prepared green sheet in a suitable shape, such as comb-shape or spiral shape, by using a metallic paste. The metallic paste contains platinum (Pt), palladium (Pd), rhodium (Rh), gold (Au), or an alloy of any of the above metals.

Separately, secondary ceramics particles for the ceramics particles 4 are formed through granulation process, preferably using spray dryer, and scattered on that surface of the ceramics substrate 11 in the vicinity of the thick films for electrodes 12a and 12b, on which organic solvent is applied in advance. After the green sheet with the secondary particles for the ceramics particles 4 and the thick films for the electrodes 12a and 12b is sintered, a thick film for a sensor element 13 is formed by printing a paste on that surface portion of the ceramics substrate 11 having the secondary ceramics particles scattered thereon. The paste for the thick film for sensor element 13 mainly consists of gas-sensitive metal oxide powder, such as powder of titania ($TiO_2$), tin oxide ($SnO_2$), and the like, and if necessary, the paste may contain noble metal powder. Then, the thick film of the paste made of gas-sensitive metal oxide is fired so as to produce the sensor element 13.

In the gas sensor of the invention thus produced, the sensor element 13 is very strongly bonded to the ceramics substrate 11 because it is formed on a roughened portion of the substrate surface, which roughened portion is prepared by bonding the ceramics particles 4 thereto. A feature of the invention is in that the gas sensor having the sensor element 13 very strongly bonded to the substrate 11 can be produced through a very simple process without necessitating any special apparatus, because the above roughened surface portion of the substrate 11 is made by separately preparing the substrate 11 and the ceramics particles 4 through conventional means and then by sintering them after scattering the ceramics particles 4 on the desired surface zone of the ceramics substrate 11.

Figure 4:
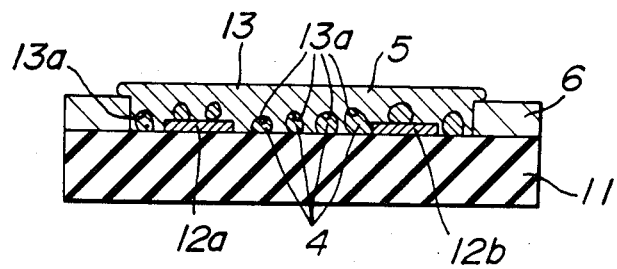
FIG. 4 is a schematic sectional view of another gas sensor according to the present invention.

FIG. 4 shows an embodiment of the invention in which a protective sheet 6 with an opening 5 is overlaid on the substrate 11 and the sensor element 13 is formed by printing a thick film therefor so as to block the opening 5. In this case, the zone where the granular ceramics particles 4 are scattered is restricted by the opening 5, so that the granular ceramics particles 4 can be easily scattered with a high degree of uniformity and the bondage of the sensor element 13 to the substrate 11 is made stronger accordingly.

Figure 3A:
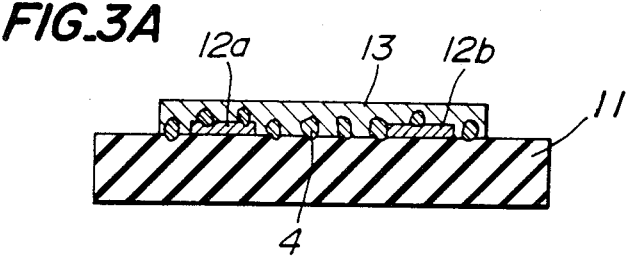
FIG. 3A is a schematic sectional view of a gas sensor using ceramics particles partially thrusted into the surface portion of a ceramics substrate.
Figure 4A:
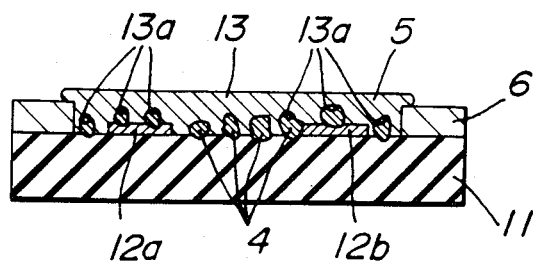
FIG. 4A is a schematic sectional view of a modification of the gas sensor of FIG. 4 in which sensor ceramic particles are partially thrusted into the surface portion of the ceramics substrate.

FIG. 3A and FIG. 4A show modified embodiments of the gas sensor of the invention, in which ceramics particles 4 are partially thrusted into the surface portion of a ceramics substrate 11. More particularly, electrodes 12a and 12b in the form of thick films are formed on a surface of the substrate 11 made of insulating sintered ceramics, and the ceramics particles 4 are scattered on the surface of the substrate 11 in the vicinity of the electrodes 12a and 12b, which ceramics particles 4 are thrusted into the surface portion of the substrate 11 by a depth corresponding to one-twentieth to one-fourth of the mean diameter thereof so that the ceramics particles 4 are integrally bonded to the substrate 11. A thick film for a sensor element 13 is printed on the surface of the substrate 11 in such a manner that the sensor element 13 is electrically connected to the electrodes 12a and 12b and strongly bonded to the substrate 11 through the ceramics particles 4.

In the gas sensor of the invention, the sensor element 13 is very strongly bonded to the ceramics substrate 11, because firstly the ceramics particles 4 bonded to the substrate provide a roughened surface to the substrate, so as to increase the contact area between the sensor element 13 and the ceramics substrate 11, and secondly the granular ceramics particles 4 engage recesses 13a (see FIG. 3) at the bottom surface of the sensor element 14 so as to bring about hook action therebetween. The ceramics particles 4 are prepared in the form of granular secondary particles of which diameters fall in the above-mentioned range before being sintered; namely, the mean diameter of the ceramics particles 4 before sintering must be at least 5 $\mu$m or more and their maximum diameter before sintering must be not larger than 500 $\mu$m or less. The roughness of the substrate surface produced by such ceramics particles 4 is much higher than that of regular substrate.

If the mean diameter of the ceramics particles 4 is smaller than 5 $\mu$m, sufficient roughness for improving the bondage cannot be achieved, while presence of excessively large ceramic particles 4 with a diameter of larger than 500 $\mu$m tends to hamper the formation of uniform thickness in printing the thick film for the sensor element 13. Besides, excessively large ceramics particles 4 tend to cause a large dispersion. A more preferable range of the size of the ceramics particles 4 is 50–200 $\mu$m.

The reason for partially thrusting the ceramics particles 4 into the surface portion of the ceramics substrate 11 by a depth corresponding to one-twentieth to one-fourth of the mean diameter thereof is in that such thrusting increases the contact area between the ceramics particles 4 and the substrate 11 so as to improve the bonding strength therebetween. If the thrusting depth is less than one-twentieth of the mean diameter of the ceramics particles 4, the desired improvement of the bonding strength cannot be achieved, while if the thrusting depth exceeds one-fourth of the above diameter, the process of thrusting becomes difficult and the above-mentioned hooking action between the thick film for the sensor element 13 and the ceramics particles 4 becomes less effective.

As to the amount of the ceramics particles 4 to be used, the above-mentioned range of the coverage ratio should be referred to; more particularly, the coverage ratio (A/B) of the surface area (A) of the insulating ceramics substrate 11 uncovered by the ceramics particles 4 in a zone where the ceramics particles 4 are scattered, as seen at right angles to the plane of the substrate 11 to the net area (B) of the ceramics particles 4 in said zone as seen at right angles to the plane of the substrate 11 should be in a range of 1:4 to 4:1. The preferable value of the coverage ratio is about 1:1.

The ceramics particles 4 are preferably made of the same material as that of the ceramics substrate 1 from the standpoint of simplicity in production. However, other insulating ceramics material may be used for the ceramics particles 4, provided that desired effect of the invention is achieved thereby. More specifically, it may be pointed out here that the most preferable material of the ceramics particles 4 is alumina from the standpoint of mechanial strength, heat resistively, insulating strength, and economy, but mullite, zirconia, and spinel may be also used as next suitable material for the ceramics particles 4.

A method for producing the gas sensor according to the invention will be described now. A green sheet for the insulating ceramics substrate 11 is prepared by making a slurry which is a mixture of electrically insulating ceramics powder and an organic binder in an organic solvent, and shaping the slurry into the green sheet by a method using a doctor blade or the like. Thick films for the electrodes 12a and 12b forming an electrode pattern are printed on a surface of the thus prepared green sheet in a suitable shape, such as comb-shape or spiral shape, by using a metallic paste. The metallic paste contains platinum (Pt), palladium (Pd), rhodium (Rh), gold (Au), or an alloy of any of the above metals.

Separately, secondary ceramics particles for the ceramics particles 4 are granulated and scattered on the surface of the ceramics substrate 11 in the vicinity of the thick films for electrodes 12a and 12b. After the above particles are pressed toward the substrate 11 so as to be partially thrusted into the substrate 11 by a depth corresponding to one-twentieth to one-fourth of the mean diameter thereof, the green sheet with the secondary particles for the ceramics particles 4 and the thick films for the electrodes 12a and 12b is sintered, and a thick film for a sensor element 13 is formed by printing a paste on that surface portion of the ceramics substrate 11 having the secondary ceramics particles scattered thereon. The paste for the thick film for sensor element 13 mainly consists of gas-sensitive metal oxide powder, such as powder of titania ($TiO_2$), tin oxide ($SnO_2$), zinc oxide (ZnO), iron oxide $Fe_2O_3$), and the like, and if necessary, the paste may contian noble metal powder. Then, the thick film of the paste made of gas-sensitive metal oxide is fired so as to produce the sensor element 13.

In the gas sensor of the invention as shown in FIG. 3A, the three constituents thereof, i.e., the substrate 11, the ceramics particles 4, and the sensor element 3, are very strongly bonded to each other, because the sensor element 13 is formed on that zone of the substrate 11 which is roughened by the ceramics particles 4 partially thrusted into the substrate 11. A feature of the invention is in that the gas sensor having the sensor element 13 very strongly bonded to the substrate 11 can be produced through a very simple process without necessitating any special apparatus, because the above roughened surface portion of the substrate 11 is made by separately preparing the substrate 11 and the ceramics particles 4 through conventional means and then by sintering them after scattering the ceramics particles 4 on the desired surface zone of the ceramics substrate 11.

FIG. 4A shows a modification of the above embodiment of the invention, in which a protective sheet 6 with an opening 5 is overlaid on the substrate 11 and the sensor element 13 is formed by printing a thick film therefor so as to block the opening 5. In this case, the zone where the granular ceramics particles 4 are scattered is restricted by the opening 5, so that the granular ceramics particles 4 can be easily scattered with a high degree of uniformity and the bondage of the sensor element 13 to the substrate 11 is made stronger accordingly.

FIG. 8 through FIG. 11 illustrate other embodiments of the gas sensor of the invention.

Figure 8:
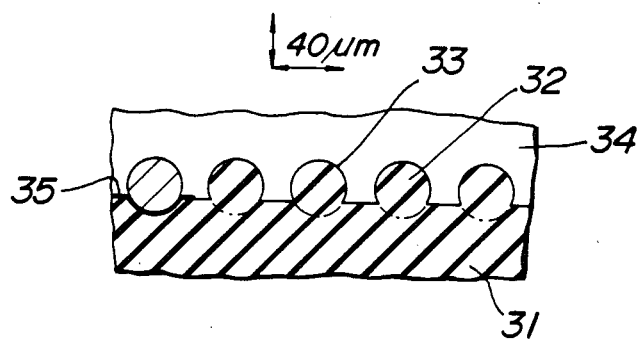
FIG. 8 is a partial sectional view of the essential portion of a substrate, shown on a large scale.

FIG. 8 schematically shows a model cross-section of the bondage between an insulating ceramics substrate 31 and a thick film 34 on an exaggerated scale. Sintered ceramics particles 32, which are spherical in the figure, are partially thrust into the surface portion of the substrate 31, so as to be integrally bonded thereto. A roughened surface 33 is formed by the thus thrusted ceramics particles 32. The thick film 34 consists of metal oxide and is deposited on the roughened surface 33 so as to fill up interstices among projections of the roughened surface 33. In the figure, an electrode layer 35 formed on the substrate 31 receives one of the ceramic particles 32 and thrusted into the substrate 31 together with the ceramics particles 32.

The regular surface of the ceramics substrate 31 has a certain roughness, for instance, as shown in the view (a) of FIG. 9. Maximum extent of artificial roughening which is applicable to the surface of the substrate 31 of electronic sensors by conventional roughening methods is, for instance, as shown in the view (b) of FIG. 9. In a preferred embodiment of the invention, for instance, spherical ceramics particles 32 with a diameter of about 30 μm are partially thrusted into the surface portion of the substrate 31 by a few microns (μm), and a greatly roughened surface 33 is formed as shown in the view (c) of FIG. 9. Thus, the method of the present invention roughens the substrate surface to a greater extent than conventional roughening method.

In the roughened surface 33 as shown in FIG. 8 and in the view (c) of FIG. 9, interstices are formed among the scattered ceramics particles 32, and such interstices somewhat expand as they extend toward the surface of the substrate 31. Accordingly, when the thick film 34 is applied to the substrate 31 so as to fill up the interstices among the scattered ceramics particles 32, the bottom portion of the thick film 34 is firmly hooked in the interstices and the thick film 34 is strongly bonded to the substrate 31.

In fact, it was actually confirmed by tests that uniform scattering and thrusting of the sintered ceramics particles 32 on the substrate surface in a zone to be covered by the thick film 34 bring about the above-mentioned firm hooking of the bottom portion of the thick film 34 by the interstices among the ceramics particles 32 even after the firing thereof.

FIG. 10A schematically shows the appearance of a gas sensor according to the invention. In the figure, electrodes 35a and 35b are formed on the surface of a ceramics substrate 31. In conventional gas sensors, a thick film for a sensor element is formed over the entire span of the electrodes 35a and 35b and fired. The sensor element thus formed in the conventional gas sensor is not firmly connected to the substrate, and changes in the internal resistance of the gas sensor has been experienced from time to time. Especially, when the conventional gas sensor is used in an atmosphere where temperature varies quickly in a cyclic manner over a wide range, such as that in an automobile engine exhaust gas passage, the difference in the coefficient of thermal expansion between the substrate 31 and such fired sensor element causes thermal strain in the sensor element, which thermal strain sometimes results in separation of the sensor element from the substrate 31. Thus, the normal function of the gas sensor is deteriorated soon after it is put into service.

The above-mentioned weak bondage between the sensor element and its substrate has been experienced not only in gas sensors but also in other functional elements using semiconductive thick films with sensor function; for instance, a thermo sensor having a thermister film coated on an insulating ceramics substrate, a humidity sensor having a humidity-sensitive element mounted on a ceramics substrate, a thick film capacitor using a dielectric film, and the like. Besides, there is a need for improvement of the bondage in other ceramics devices having films made of different ceramics materials; for instance, a ceramic body having a protective film of different material coated thereon.

Referring to FIG. 10B showing a sectional view taken along the line XB—XB of FIG. 10A, the present invention uses a roughened surface 33 formed by substantially uniformly scattering sintered ceramics particles 32 on the surface of the substrate 31 and partially thrusting the ceramics particles 32 into the surface portion of the substrate 31 so as to integrally connect the particles 32 to the substrate 31. The thick film 34 for a sensor element is applied to the surface of the substrate 31 while filling interstices among projections of the roughened surface 33 with the thick film 34. Upon firing, the bottom portion of the thick film 34 is firmly bonded to the roughened surface 33 by hook action between the above projections and the thick film bottom portion intruding into interstices among such projections. The bondage between the thick film 34 and the substrate 31 is greatly improved.

In the embodiment illustrated in FIG. 11, a respective sheet 36 having an opening 37 is overlaid on the ceramics substrate 31. The zone for scattering the ceramics particles 32 is restricted to the opening 37, so that the scattering of the ceramics particles 32 can be effected easily and uniformly.

The invention will be described in further detail now by referring to examples.

EXAMPLE 1

A slurry was prepared by dissolving in an organic solvent 100 parts by weight of powder mixture consisting of 92 wt % of alumina ($Al_2O_3$), 4 wt % of silica ($SiO_2$), 2 wt % of calcia (CaO), and 2 wt % of magnesia (MgO), the powder mixture having a mean diameter of 1.5 μm, 12 parts by weight of butyral resin, and 6 parts by weight of dibutyl phthalate (DBP). Referring to FIG. 5 and FIG. 6, a 1 mm thick greet sheet 21 and a 0.2 mm thick green sheet 7 were formed from the thus prepared slurry by using a doctor blade. A heater resistor pattern 8 and electrode patterns 22a and 22b were printed on the green sheet 21 in the form of thick film by using a platinum paste as shown in FIG. 5. Terminals 9a, 9b and 9c were made by using a platinum wire of 0.3 mm diameter and connected to the resistor pattern 8 and the electrode patterns 22a and 22b, as shown in FIG. 5. An opening 5 is bored through the other green sheet 7 at such position that free ends of the electrode patterns 22a and 22b on the green sheet 21 could be exposed when the green sheet 7 was overlaid on the green sheet 21. The two green sheets 21 and 7 were superposed and bonded to each other by pressing and heating.

Separately, granules for the ceramics particles 4 were prepared by adding 4 parts by weight of polyvinyl alcohol to the same powder mixture with the same chemical composition as that for the above green sheets, granulating the powder mixture added with the polyvinyl alcohol into sperical granules by spray drying, and sieving the spherical granules into grain size classes as shown in Table 1.

The granules thus prepared were scattered on the green sheet 21 through the opening 5 at the above-mentioned coverage ratio of 1:1, and the granules were partially thrusted into the surface portion of the green sheet 21 by pressing the granules through a cushion sheet with a pressure of 8 kg/cm² at 50° C.

The pressure bonded green sheets 21 and 7 carrying the thrusted granules for the ceramics particles 4 were fired at 1,500° C. for two hours in air.

The hardness of the above granules before the sintering could be increased to a suitable level by increasing the amount of the binder therein. To facilitate the handling thereof, the granules may be heated to a temperature below the starting point of sintering thereof so as to harden them by using a small amount of glass components contained therein.

A titania paste for the sensor element 13 was prepared by adding one molar part of platinum black into titania (TiO$_2$) powder with a mean particle diameter of 1.2 μm, adding three parts by weight of ethyl cellulose to the entire powder, kneading the mixture in butyl carbitor, and adjusting the viscosity thereof at 300 poises. A sensor element 13 was formed by printing the titania paste on the green sheet 21 as a thick film in contact with the free ends of the electrode patterns 22a and 22b while blocking the opening 5 of the green sheet 7 with the thick film, and firing the green sheets with the titania paste thick film printed thereon at 1,200° C. for one hour in air.

Gas sensors No. 1 through No. 8 as shown in FIG. 7 were prepared by repeating the above procedures under the specific conditions as described in Table 1. However, the gas sensor No. 1 was made by forming the sensor element 13 without scattering the ceramic particles 4 on the green sheet 21 through the opening 5.

The internal resistance of the gas sensors No. 1 through No. 8 was measured in an atmosphere at 350° C. heated by a propane burner. At a theoretical air-fuel ratio of larger than 1 ($\lambda > 1$), the internal resistance was larger than 200 MΩ for all the gas sensors. When the air-fuel ratio was kept at 0.9 ($\lambda = 0.9$), the internal resistance varied as shown in Table 1. Thus, all the gas sensors of the invention proved to fulfil the function of the gas sensor.

Repetitive thermal impact tests were applied to the gas sensors by cyclically exposing them to exhaust gas with a maximum temperature of 800° C. from a fully loaded engine with a displacement of 2,000 cc for five minutes and to exhaust gas from the engine under idling condition for five minutes. The time until the sensor element 13 was separated from the substrate 21 was measured. The result is shown in Table 1.

TABLE 1

| Gas sensor No. | Reference or invention | Diameter range of ceramics particles 4 (μm) | Internal* resistance (kΩ) | Time until separation (hour) |
| --- | --- | --- | --- | --- |
| 1 | reference | — | 42 | 8 |
| 2 | " | >5 | 40 | 10 |
| 3 | invention | 5–43 | 35 | 40 |
| 4 | " | 43–104 | 42 | 120 |
| 5 | " | 104–175 | 38 | >500 |
| 6 | " | 175–417 | 51 | >500 |
| 7 | reference | 417–991 | 85 | >500 |
| 8 | " | 991–1650 | 150 | >500 |

*Internal resistance represents the internal resistance of the gas sensor measured at 350° C. in an atmosphere with an air-fuel ratio $\lambda = 0.9$.

As can be seen from Table 1, gas sensors No. 3 through No. 6 according to the invention had a much stronger bondage of the sensor element 13 to the substrate 21 as compared with that of the reference gas sensors No. 1 and No. 2. Other reference gas sensors No. 7 and No. 8 had a bondage as strong as that of the invention, but the printing of the sensor element 13 was not uniform.

EXAMPLE 2

The bonding strength between the substrate 21 and the ceramics particles 4 was tested by preparing Specimens No. 1 through No. 6. All the Specimens were made in the same manner as the above-mentioned gas sensor No. 4 of Example 1 except the following two points; namely, a point that the ceramics particles 4 were bonded to the green sheet 21 under the conditions of Table 2, and another point that no sensor element 13 was made at the opening 5 after the sintering of the green sheets 21 and 7.

The impact test as stipulated in the Japanese Industrial Standard (JIS) B8031-1974 was applied to the Specimens No. 1 through No. 6, so as to check the relationship between the trusting rate and the separation rate. The result is shown in Table 2.

TABLE 2

| Specimen No. | Reference or invention | Temperature (°C.) | Pressure (kg/cm$^2$) | Thrust-* ing rate (%) | Separation rate (%) |
| --- | --- | --- | --- | --- |
| 1 | reference | rm temp | 0 | 1.1 | 12.1 |
| 2 | " | 50 | 3 | 3.5 | 8.3 |
| 3 | invention | 40 | 7 | 5.2 | 1.0 |
| 4 | " | 50 | 8 | 12.0 | 0.5 |
| 5 | " | 50 | 15 | 22.6 | 0.2 |
| 6 | reference | 80 | 15 | 28.0 | 0.2 |

*Thrusting rate was determined by observing the cross-section of the substrate through a microscope, arbitrarily selecting five ceramics particles, measuring the diameter d$_1$ and the thrusted depth d$_2$ of each selected ceramics particle, determining a value of thrusting rate (d$_2$/d$_1$) × 100 for each of the selected ceramics particles, and taking the average of the five values.

As can be seen from Table 2, Sepcimens No. 3 through No. 5 coming under the scope of the invention with a thrusting rate of one-twentieth to one-fourth (5% to 25%) had a small separation rate, and strong bondage of the invention was proved. Specimens No. 1 and No. 2 with a thrusting rate of smaller than one-twentieth (5%) showed large separation rates. In the case of Specimen No. 6 with a thrust rate of larger than one-quarter (25%), most of the granular ceramics particles were broken in the process of thrusting, and the work was very difficult.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

We claim:

1. A gas sensor comprising an electrically insulating substrate made of sintered ceramics, thick film electrodes formed on a surface of said substrate, sintered ceramics particles scattered onto, integrally bonded to and extending outwardly from the surface of said substrate in the vicinity of said thick film electrodes, said sintered ceramics particles having a granulated mean diameter of at least 5 μm and a granulated maximum diameter of not larger than 500 μm before being sintered, and a sensor element in the form of a thick film firmly bonded to the surface of said substrate through said scattered ceramics particles, to said thick film electrodes to be electrically connected therewith, and to said scattered ceramics particles.

2. A gas sensor comprising an electrically insulating substrate made of sintered ceramics, thick film electrodes formed on said substrate, sintered ceramics particles scattered onto, integrally bonded to and extending outwardly from a surface of said substrate in the vicinity of said thick film electrodes, said sintered ceramics particles having a granulated mean diameter of at least 5 μm and a granulated maximum diameter of not larger than 500 μm before being sintered, each of said sintered ceramics particles extending into said substrate below the surface thereof by one-twentieth to one-fourth of the mean diameter of said particles, and a sensor element in the form of a thick film firmly bonded to said substrate through said scattered ceramics particles, to said thick film electrodes to be electrically connected therewith and to said scattered ceramics particles.

3. A ceramics substrate carrying a metal oxide thick film comprised of an electrically insulating ceramics substrate, a roughened surface formed on said substrate defined by scattered ceramics particles partially extending into said substrate and bonded to said substrate, and a metal oxide thick film sintered onto said roughened surface filling up the interstices between the projections of the scattered ceramics particles and bonded to said substrate.

* * * * *